United States Patent [19]
Konig et al.

[11] Patent Number: 5,466,669
[45] Date of Patent: Nov. 14, 1995

[54] IMMUNOSTIMULATORY AGENT

[75] Inventors: Wolfgang Konig, Bochum, Germany; Mamoru Tomita; Seiichi Shimamura, both of Yokohama, Japan; Kozo Kawase, Urawa, Japan; Mitsunori Takase, Omiya, Japan; Wayne R. Bellamy, Zama, Japan

[73] Assignee: Morinaga Milk Industry Co., Ltd., Tokyo, Japan

[21] Appl. No.: 971,981

[22] PCT Filed: Mar. 7, 1992

[86] PCT No.: PCT/JP92/00275
§ 371 Date: Feb. 19, 1993
§ 102(e) Date: Feb. 19, 1993

[87] PCT Pub. No.: WO93/18061
PCT Pub. Date: Sep. 16, 1993

[51] Int. Cl.[6] ............................. A61K 38/00; C07K 5/00; C07K 7/00; C07K 17/00
[52] U.S. Cl. ............................................. 514/12; 530/324
[58] Field of Search ............................... 514/12; 530/324

[56] References Cited

FOREIGN PATENT DOCUMENTS 0438750  7/1991  European Pat. Off. .

OTHER PUBLICATIONS

Zimecki et al., *Chem. Abstrs*, vol. 116, No. 5, 1992, Abst No: 39616u.
Zimecki et al, *Chem Abstrs*, vol. 108, No. 13, 1988, Abst. No. 110658b.

*Primary Examiner*—Jill Warden
*Assistant Examiner*—A. M. Davenport
*Attorney, Agent, or Firm*—Wenderoth, Lind & Ponack

[57] ABSTRACT

There is disclosed an immunostimulatory agent comprising a peptide derived from lactoferrin having activity to modulate the release of inflammatory mediators from cells of the immune system. The peptide promotes the release of leukotriene B4 from polymorphonuclear neutrophils induced by activators such as the calcium ionophor A23187, It also promotes the release of histamine from mast cells induced by activators such as α-toxin-producing *Staphylococcus aureus* cells or the calcium ionophor A23187. The peptide is effective at low concentrations within the range of 1 to 100 ppm. By promoting the release of such inflammatory mediators the peptide can potentiate the cellular immune response and stimulate the host defense against infectious disease. This newly discovered immunostimulatory agent is useful as an active component of pharmaceuticals, hygiene products, clinical foods, etc., for prevention and treatment of bacterial, fungal, and viral infectious in humans and animals.

11 Claims, No Drawings

IMMUNOSTIMULATORY AGENT

TECHNICAL FIELD

This invention relates to an immunostimulatory agent comprising a peptide derived from lactoferrin having activity to modulate the release of inflammatory mediators from cells of the immune system and thereby potentiate the cellular immune response. In particular, the present invention relates to a peptide derived from lactoferrin having at least the following activities: (1) promotes the release of leukotriene B4 from polymorphonuclear neutrophils; (2) promotes the release of histamine from mast cells.

BACKGROUND ART

Polymorphonuclear neutrophils and mast cells play major role in the host defense against bacterial, fungal and viral infections. Microorganisms or their products, can interact directly with these cells and induce the release of inflammatory mediators such as leukotrienes and histamine which have multiple effects essential to amplification and control of the inflammatory response. Leukotriene B4 is a potent chemotactic and chemokinetic factor which attracts neutrophils, eosinophils, monocytes and macrophages to sites of infection and tissue trauma. It promotes the aggregation of neutrophils, augments their adherence to endothelial cells, stimulates the release of lysozomal enzymes and the production of superoxide. It also inhibits the proliferation of lymphocytes via the induction of suppressor T cells and augments cytotoxic and natural killer cell activities. On the other hand, leukotrienes C4, D4, and E4 are the slow-reacting substances of anaphylaxis which cause long-lasting contraction of smooth muscle, bronchoconstriction, vasoconstriction, secretion of mucous, and an increase in vascular permeability. Histamine induces vasodilation, increase in vascular permeability, stimulation of secretory glands and contraction of smooth muscle. Furthermore, histamine modulates certain immune effector functions such as cell-mediated cytotoxicity, lymphocyte proliferation, lymphokine production, and immunoglobulin synthesis. In general, the biological actions of leukotriene B4 and histamine tend to potentiate the cellular immune response and stimulate the host defense against microbial infections.

It is widely recognized that the biological actions of leukotriene B4 relating to recruitment and stimulation of neutrophils are essential for the host defense against microbial infections. The migration of polymorphonuclear neutrophils from circulating blood to the focus of infection is one of the earliest events of the inflammatory process. The cells leave the circulation and are guided towards sites of infection and tissue trauma by chemotaxis, in response to chemotactic factors released in the vicinity of invading microorganisms. Leukotriene B4 is the most potent chemotactic stimulus for neutrophils. The chemotactic stimulus promotes cellular movement and enables a variety of subsequent steps essential to the host defense including attachment, engulfment, ingestion, degranulation, secretion of lysozomal enzymes into phagolysozomes, and generation of toxic oxygen radicals, which ultimately lead to killing of invading microorganisms. Neutrophils control the concentration of leukotriene B4 in their environment by generating and metabolizing this inflammatory mediator. Leukotriene B4 is bound by specific receptors on the cell surface, internalized, and enzymatically oxidized producing biologically inactive products, 20-OH-leukotriene B4 and 20-COOH-leukotriene B4. In the case of major injuries, such as severely burned patients, the chemotactic responsiveness of neutrophils is impaired. Their production and release of leukotriene B4 is diminished, the metabolism of leukotriene B4 to inactive 20-OH-leukotriene B4 and 20-COOH-leukotriene B4 is enhanced, and the expression of leukotriene B4 receptors on the cell surface is reduced. Decreased production of leukotriene B4 and reduced responsiveness to leukotriene B4 leads to inadequate recruitment of phagocytes at sites of tissue injury and precedes the onset of microbial invasion.

Lactoferrin is an iron-binding glycoprotein present in various biological fluids of mammals including milk, saliva, tears and mucous secretions, and released from activated polymorphonuclear neutrophils at sites of inflammation. Large quantities of bovine lactoferrin can be obtained by extracting this protein from raw skim milk or cheese whey originating from the milk of cows and, consequently, bovine lactoferrin is readily available as a commercial product of the dairy industry. In its iron-free state, lactoferrin exhibits broad-spectrum antimicrobial activity which is commonly attributed to its ability to chelate iron and produce an iron-deficient environment limiting microbial growth. The present inventors first discovered that peptides having more potent antimicrobial properties than lactoferrin are generated upon enzymatic digestion of this protein (Japanese Patent Application No.238364/90). The antimicrobial peptide derived from lactoferrin appears to function by a mechanism distinct from iron binding and is effective at low concentrations against various species of Gram-negative and Gram-positive bacteria, yeasts, and molds, including strains known to cause disease in humans and animals. The effect of this peptide against microorganisms is lethal causing a rapid loss of colony-forming ability. Considerable potential exists for the widespread commercial use of this peptide as a safe and effective antimicrobial agent and a novel process has been established for its large-scale manufacture as described in Japanese Patent Application No.150604/91.

It has been demonstrated that lactoferrin has activity to inhibit calcium ionophore-induced release of histamine from peritoneal mast cells [Theobald, K. et. al. (1987) Agents and Actions 20:10–16], however, the effect of lactoferrin on the release of other inflammatory mediators such as leukotrienes is unknown. Whether peptides derived from lactoferrin have activity to modulate the release of inflammatory mediators from cells of the immune system has not been studied previously.

The present inventors investigated for the first time the effects of peptides derived from lactoferrin on the release of inflammatory mediators from cells of the immune system. Surprisingly, they discovered that the antimicrobial peptide of lactoferrin described in Japanese Patent Application No.238364/90 is an immunostimulatory peptide having excellent activity to modulate the release of leukotriene B4 and histamine from polymorphonuclear neutrophils and mast cells, respectively, and thereby potentiate the cellular immune response. In contrast, lactoferrin does not exhibit such useful immunostimulatory activity.

DISCLOSURE OF THE INVENTION

This invention is based on the discovery of a peptide derived from lactoferrin having the capability to modulate the release of inflammatory mediators from cells of the immune system and thereby potentiate the cellular immune response of humans and animals.

It is an object of the present invention to provide an immunostimulatory agent comprising a peptide derived from lactoferrin.

It is another object of the present invention to provide an immunostimulatory composition containing a peptide derived from lactoferrin as an active ingredient.

These objects of the present invention are achieved herein by providing an immunostimulatory peptide derived from lactoferrin having at least the following activities: (1) promotes the release of leukotriene B4 from polymorphonuclear neutrophils; (2) promotes the release of histamine from mast cells.

BEST MODE FOR CARRYING OUT THE INVENTION

The peptide of the present invention can be produced by hydrolysis of lactoferrin or generated by conventional methods of peptide synthesis and purified. Briefly, for example, a preferred method for obtaining the peptide of the present invention is as follows. Bovine lactoferrin isolated from skim milk or cheese whey is dissolved in distilled water at a concentration of 5% (w/v) and the pH is adjusted to 3.0 by addition of 1N HCl. Pepsin is added to a final concentration of 3% (w/w of substrate) and hydrolysis is performed at 37° C. for 4 h. The reaction is terminated by heating at 80° C. for 15 min and the pH of the resulting peptide mixture is adjusted to 7.0 by addition of 1N NaOH. Any insoluble peptides are removed from the starting material by filtration or centrifugation. The active peptide is purified from the resulting solution, for example, by contacting the solution with a butyl moiety-containing hydrophobic interaction chromatography medium, such as Butyl-Toyopearl 650M (Tosoh, Japan), rinsing the medium with water to remove unbound peptides, desorbing the immunostimulatory peptide at a constant pH, preferably pH 4.8–5.2, and desalting the product. Desalting can be accomplished, for example, using the same column of Butyl-Toyopearl 650M. The solution containing the peptide is adjusted to pH 7.0, by addition of 1N NaOH, and contacted with the hydrophobic medium. The medium is rinsed with water to remove the buffer salts and finally the active peptide is desorbed with 10 mM HCl and freeze-dried. Accordingly, the peptide of the present invention can be obtained in greater than 99% purity, free of all other biologically active substances, in any desired quantity.

The present inventors have succeeded in isolating and purifying a peptide of bovine lactoferrin with defined nature and function and subsequently have succeeded in demonstrating for the first time its activity to modulate the release of potent inflammatory mediators from cells of the immune system. For instance the peptide of the present invention consists of a single chain of amino acids having the sequence Phe-Lys-Cys-Arg-Arg-Trp-Gln-Trp-Arg-Met-Lys-Lys-Leu-Gly-Ala-Pro-Ser-Ile-Thr-Cys-Val-Arg-Arg-Ala-Phe (SEQ ID No. 1). It is the same peptide of lactoferrin described in Japanese Patent Application No.238364/90 having broad spectrum antimicrobial activity. That is, the peptide of the present invention has both immunostimulatory and antimicrobial properties. In the specification of the present invention, the amino acids and peptides are represented by the abbreviations employed by IUPAC-IUB Committee on Biochemical Nomenclature, such as the following abbreviations:

Ala-: L-Alanine residue
Arg-: L-Arginine residue
Asn-: L-Asparagine residue
Asp-: L-Aspartic acid residue
Cys-: L-Cysteine residue
Gln-: L-Glutamine residue
Glu-: L-Glutamine acid residue
Gly-: Glycine residue
His-: L-Histidine residue
Ile-: L-Isoleucine residue
Leu-: L-Leucine residue
Lys-: L-Lysine residue
Met-: L-Methionine residue
Phe-: L-Phenylalanine residue
Pro-: L-Proline residue
Ser-: L-Serine residue
Thr-: L-Threonine residue
Trp-: L-Tryptophan residue
Tyr-: L-Tyrosine residue
Val-: L-Valine residue In consideration of the fact that lactoferrins of mammalian species are well known to exhibit a high level of amino acid sequence homology, it is now obvious as a result of their discovery that immunostimulatory peptides having substantially the amino acid sequence of the peptide of the present invention, but having minor substitutions of amino acids which do not abolish its immunostimulatory properties, may be produced by hydrolysis of lactoferrins of other mammals such as human, water buffalo, sheep, goat, etc. Furthermore, it is now obvious as the result of their discovery that immunostimulatory peptides having substantially the amino acid sequence of the peptide of the present invention, but having minor deletions, additions, or substitutions of amino acids or other minor chemical modifications which do not abolish its immunostimulatory properties, may be produced by conventional methods of peptide synthesis. Such obvious peptides are contemplated and should not be considered as being novel or distinct from the present invention.

The peptide so obtained has at least the following immunostimulatory activities: (1) promotes the release of leukotriene B4 from polymorphonuclear neutrophils; (2) promotes the release of histamine from mast cells. These useful activities can be readily demonstrated, for example, by the procedures described in detail later in this specification (see Test 1–3). By promoting the release of such potent inflammatory mediators from neutrophils and mast cells the peptide of the present invention can potentiate the cellular immune response and stimulate the host defense against infectious disease. Most importantly, its activity to promote the release of leukotriene B4 from neutrophils can enhance the recruitment and stimulation of phagocytes at sites of infection and tissue trauma and thereby promote the destruction of invading microorganisms. Such activity may be especially beneficial in the case of major injuries, such as severely burned patients, in which polymorphonuclear neutrophils display diminished production of leukotriene B4 and reduced responsiveness to leukotriene B4.

The immunostimulatory peptide so obtained is included as an active ingredient at a concentration of at least 1 ppm and preferably 10 to 100 ppm in order to obtain the immunostimulatory composition of the present invention.

The compositions may contain pharmaceutically suitable solvents (e.g. water, ethanol, glycerol, propylene glycol, liquid polyethylene glycol), flavoring agents, sweetening agents, binders, isotonic agents, coating agents, surfactants, absorption delaying agents, and the like. The use of such agents is well known in the art. Except insofar as any conventional media or agent is incompatible with the active ingredient, its use in the compositions is contemplated. Supplementary active ingredients can also be incorporated into the compositions. Of course, any material used in preparing the compositions should be non-toxic in the amounts employed.

The peptide of the present invention can be administered to humans or animals, for example, dermatologically, ophthalmically, otically, nasally, anally, or vaginally as a powder or as a component of a solution, suspension, cream, ointment, or spray. The peptide may also be orally administered, for example, as a powder or aqueous solution, or it may be incorporated into capsules, tablets, syrups, elixers, or the like, or it may be incorporated directly into food of the diet. The peptide may also be administered, for example, parenterally, intraperitoneally or intramuscularly as a component of a sterile injectable solution.

The peptide of the present invention can be used, for example, in medicinal pharmaceutical products (such as eye medications, mastitis medications, athlete's foot medications), non-medicinal pharmaceutical products (such as mouth washes), various cosmetic products (such as skin lotions and creams), various food products (such as chewing gum), it can be also be added to, compounded with, sprayed onto, adhered to, or used for coating or impregnation of any and all products wherein its immunostimulatory activity is desired (such as surgical dressings, bandages, etc.) or otherwise used for treating any and all products wherein its immunostimulatory activity is desired.

The present invention is further described by means of the following Tests.

TEST 1

This test was performed to study the activity of the peptide of the present invention to promote the release of histamine from rat peritoneal mast cells induced by the calcium ionophore A23187.

(1) Sample Preparation

Peritoneal cells were collected from Wistar rats after intraperitoneal injection of phosphate-buffered saline (consisting of 120 mM NaCl, 10 mM $Na_2PO_4$, 3 mM $KH_2PO_4$, pH 7.4). Their abdoments were massaged and the buffer containing the cells was recovered. The cells were centrifuged at 300×g for 15 min and washed twice with phosphate-buffered saline. The cells from several rats were pooled for use in the experiments.

(2) Experimental Methods

Rat peritoneal cells containing about $1 \times 10^5$ mast cells per ml were used as the target cells. A 500 µl volume of the cell suspension was incubated with 100 µl volume of the test substance [purified peptide obtained by the method as in Example 1, or human lactoferrin (Sigma Chemical Co.), or bovine lactoferrin (Morinaga Milk industry Co.)] at 37° C. for 30 min. Thereafter, histamine release from the mast cells was induced by the addition of calcium ionophore A23187 (Sigma Chemical Co.) at a final concentration of 5 µM. After 10 min of incubation the cells were centrifuged at 300×g for 15 min and the supernatant was removed and deproteinized by the addition of 2 ml of $HClO_4$ (2%). The deproteinized sample was then centrifuged at 2000×g for 20 min and the histamine content in the supernatant was determined by the fluorophotometric analyser technique (AutoAnalyzer: Technikon). Cells in the presence of phosphate-buffered saline served as control.

(3) Results

The experimental data shown in Table 1 indicate that the peptide of the present invention has activity to promote the release of histamine from mast cells induced by the calcium ionophore A23187. It exhibits such activity at low concentrations within the range of 1 to 100 ppm, and the amount of histamine released increases in a dose dependent manner depending on the concentration of the peptide. On the other hand, the results further indicate that human and bovine lactoferrins show little, if any, such activity.

TABLE 1

| Treatment | ppm | Histamine release (Relative %) |
| --- | --- | --- |
| control (saline) | — | 100 |
| purified peptide | 1 | 135 ± 10 |
|  | 10 | 145 ± 15 |
|  | 100 | 175 ± 20 |
| lactoferrin, human | 1 | 115 ± 20 |
|  | 10 | 110 ± 10 |
|  | 100 | 100 ± 10 |
| lactoferrin, bovine | 1 | 105 ± 25 |
|  | 10 | 110 ± 20 |
|  | 100 | 125 ± 25 |

TEST 2

This test was performed to study the activity of the peptide of the present invention to promote the release of histamine from rat peritoneal mast cells induced by α-toxin-producing Staphylococcus aureus cells.

(1) Sample Preparation

Staphylococcus aureus 121, an α-toxin-producing strain, was cultured overnight in Brain Heart Infusion broth at 37° C. The bacterial cells were collected by centrifugation at 4000×g for 20 min, washed with phosphate-buffered saline, and suspended in the same buffer for use in the experiment. Rat peritoneal cells were prepared as in Test 1.

(2) Experimental Method

The same method as in Test 1 was used, except histamine release from the mast cells was induced by the addition of α-toxin-producing Staphylococcus aureus cells at a final concentration of about $1.0 \times 10^8$ cells per ml.

(3) Results

The experimental data shown in Table 2 indicate that the peptide of the present invention has activity to promote the release of histamine from mast cells induced by α-toxin-producing Staphylococcus aureus cells. It exhibits such activity at low concentrations within the range of 1 to 100 ppm, and the amount of histamine released increases in a dose dependent manner depending on the concentration of the peptide. On the other hand, the results further indicate that human and bovine lactoferrine shown little, if any, such activity.

TABLE 2

| Treatment | ppm | Histamine release (Relative %) |
| --- | --- | --- |
| control (saline) | — | 100 |
| purified peptide | 1 | 200 ± 60 |
|  | 10 | 250 ± 50 |
|  | 100 | 460 ± 240 |
| lactoferrin, human | 1 | 180 ± 5 |
|  | 10 | 115 ± 15 |
|  | 100 | 120 ± 20 |
| lactoferrin, bovine | 1 | 150 ± 10 |
|  | 10 | 160 ± 10 |
|  | 100 | 110 ± 15 |

TEST 3

This test was performed to study the activity of the peptide of the present invention to promote the release of leukotriene B4 from human polymorphonuclear neutrophils induced by the calcium ionophore A23187.

(1) Sample Preparation

Human polymorphonuclear neutrophils were prepared by fractionation of leukocytes from heparinized blood of healthy donors on a Ficoll-metrizoate gradient followed by dextran sedimentation. The cells were centrifuged at 300×g, and washed three times with phosphate-buffered saline, after which less than 2% of the platelets remained. Erythrocytes were removed by exposing the cells to hypotonic conditions. The purity of the polymorphonuclear neutrophil fraction used was greater than 97% as confirmed by light microscopy.

(2) Experimental Method

For analysis of leukotriene release, human neutrophils suspended in phosphate-buffered saline at approximately $1\times10^7$ cells per ml were used as the target cells. The cells were incubated for 30 min in the presence of test substance [(purified peptide obtained by the method as in Example 1, or human lactoferrin (Sigma Chemical Co.), or bovine lactoferrin (Morinaga Milk Industry Co.)]. Leukotriene release from the neutrophils was then induced by the addition of calcium ionophore A23187 (Sigma chemical Co.) at a final concentration of 5 µM. After 30 min, the supernatants of the stimulated cells were deproteinized by addition of 2 ml of methanol-acetonitrile (1:1) overlaid with nitrogen and frozen for 12 h at −70° C. After centrifugation at 1000×g for 15 min the supernatant was evaporated to dryness in a freeze dryer, suspended in 0.5 ml of methanol-water (30:70), overlaid with nitrogen, and stored overnight at −70° C. The samples were centrifuged at 1000×g and the supernatant was assayed for the presence of leukotrienes by high pressure liquid chromatography using a reverse-phase column of Nucleosil (C18; 5 µm particles) at a column temperature of 40° C. The solvent system was a mixture of phosphate buffer (17 mM $K_2HPO_4$ containing 0.05% EDTA), acetonitrile, and methanol (50:30:20) adjusted to pH 5.0 with phosphoric acid. The absorbance at 280 nm of the column effluent was monitored and recorded. The concentration of each eluted leukotriene was determined from the peak area by means of a computing integrator. The leukotrienes were identified from their retention times with reference to known standards. The minimum detectable quantity was 1 ng in each instance. Because leukotriene B4 is rapidly metabolized by neutrophils to the biologically inactive products 20-OH-leukotriene B4 and 20-COOH-leukotriene B4 under the conditions of this experiment the total amount of leukotriene B4 released includes the sum of these inactive products.

(3) Results

The experimental data shown in Table 3 indicate that the peptide of the present invention promotes the release of leukotriene B4 from polymorphonuclear neutrophils. It exhibits such activity at low concentrations within the range of 1 to 100 ppm, and the amount of leukotriene B4 released increases in a dose-dependent manner depending on the concentration of the peptide. On the other hand, the results further indicate that human and bovine lactoferrins have little, if any, such activity. None of the compounds tested substantially promotes the release of the spasmogenic leukotriene C4.

TABLE 3

| Treatment | ppm | Leukotriene released (ng) | | | | |
|---|---|---|---|---|---|---|
| | | B4 | 20-OH | 20-COOH | (Total B4) | C4 |
| control (saline) | — | 12 | 55 | 31 | (98) | 18 |
| purified peptide | 1 | 12 | 70 | 51 | (133) | 23 |
| | 10 | 14 | 116 | 61 | (191) | 17 |
| | 100 | 18 | 162 | 104 | (284) | 23 |
| lactoferrin, human | 1 | 11 | 80 | 41 | (131) | 12 |
| | 10 | 10 | 50 | 26 | (86) | 13 |
| | 100 | 10 | 42 | 26 | (76) | 17 |
| lactoferrin, bovine | 1 | 9 | 50 | 41 | (100) | 17 |
| | 10 | 11 | 60 | 36 | (107) | 15 |
| | 100 | 11 | 59 | 35 | (105) | 15 |

The following examples are merely illustrative of the invention.

EXAMPLE 1

Production of the peptide of the present invention is exemplified as follows. Bovine lactoferrin (2.0 kg: Morinaga Milk Industry Co., Ltd; purity, approximately 90%) isolated from skim milk was dissolved in distilled water at a concentration of 5% (w/v) and the pH was adjusted to 3.0 by addition of 1N HCl. Crystalline pepsin (Difco Laboratories) was added to a final concentration of 3% (w/w of substrate) and hydrolysis was performed at 37° C. for 4 h. The reaction was terminated by heating at 80° C. for 15 min. The pH of the resulting peptide mixture was adjusted to 7.0 by addition of 1N NaOH and insoluble peptides were removed by filtration. The peptide solution was spray-dried to obtain 1.9 kg of powdered material. A 600 g portion of the powdered material was dissolved in distilled water at a final concentration of 5% (w/v). Butyl-Toyopearl 650M (Tosoh Corp.) was rinsed and equilibrated with water before use and approximately 3.0 liters of this hydrophobic gel were used. The starting material was initially contacted with the hydrophobic medium in a stirred tank, then the liquid was collected and the medium was transferred to a chromatographic column (10 cm×20 cm i.d.). The collected liquid was again contacted with the medium in the column, then the hydrophobic medium was rinsed with water, at a flow rate of about 400 ml/min, to remove the unbound peptides. Rinsing of the medium was continued until the protein content of the water eluted from the medium declined to a low level, as indicated by an absorbance at 280 nm of about 0.06. The bound peptides including the immunostimulatory peptide were desorbed from the medium with 10 mM HCl and mixed with an equal volume of McIlvaine buffer, pH 7.0 (prepared by combining solutions of 0.1 M citric acid and 0.2M $Na_2HPO_4$ in a ratio of 177:824). The resulting buffered peptide solution was contacted with the hydrophobic medium and the medium was rinsed with about 6 liters of the same buffer. The active peptide was desorbed selectively from the medium at a constant pH with about 9 liters of McIlvaine buffer, pH 5.0 (prepared by combining solutions of 0.1M citric acid and 0.2M $Na_2HPO_4$ in a ratio of 485:515). Desalting of the solution thus obtained was accomplished using the same 3000 ml of Butyl-Toyopearl 650M. The solution was adjusted to pH 7.0, by addition of 1N NaOH, and contacted with the hydrophobic medium, then the medium was rinsed with about 30 liters of water to remove the buffer salts. Finally, active peptide was desorbed with 10 mM HCl and freeze-dried to obtain 10.5 grams of powdered product. The purity of the product was greater than 99% as estimated by reverse-phase high performance liquid chromatography.

EXAMPLE 2

Production of the peptide of the present invention is further exemplified as follows. The peptide was chemically synthesized using an LKB Biolynk model 4170 automated peptide synthesizer (manufactured by Pharmacia LKB Biotechnology Co.). 390 mg of Fmoc-phenylalanine anhydride were fixed to Ultrosyn A resin (manufactured by Pharmacia LKB Biotechnology Co.) through the carboxyl group using dimethylaminopyridine as a catalyst. Next, the resin was washed with dimethylformamide containing piperidine and the protecting group of the amine functional group of the C-terminal amino acid was removed. 156 mg of Fmoc-alanine anhydride of the second amino acid residue from the C-terminus were then coupled to the unprotected amine group of the above-mentioned phenylalanine residue. Subsequently the successive desired amino acids were fixed in the same manner, except for cysteine in which an acetamidomethylated Fmoc-amino acid was used, coupling of a phenylalanine residue which was the 25th from the C-terminal was completed and a peptide chain of the desired amino acid sequence was formed. Next the protective groups were removed and the peptide was released with a solvent (composed of 94% trifluoroacetic acid, 5% phenol and 1% ethandiol), the peptide was purified by high-performance liquid chromatography, vacuum-dried, and about 150 mg of acetoamidomethylated peptide were obtained. These 150 mg of acetoamidomethylated peptide were dissolved in 10 ml of 90% acetic acid aqueous solution, 2.5 ml of 1M hydrochloric acid were added, the solution was vigorously stirred for 30 minutes, 5 ml of 1M sodium thiosulfate aqueous solution were added and the reaction was stopped, and the solution was concentrated to about 40 ml with a rotary evaporator. This concentrated solution was purified using a Sephadex G15 (manufactured by Pharmacia Co.) column (50×500 mm), vacuum-dried, and about 70 mg of the immunostimulatory peptide were obtained.

EXAMPLE 3

20 mg of the immunostimulatory peptide obtained by the same method as in Example 1 were dissolved in 1000 ml of purified water, and an immunostimulatory agent was produced.

EXAMPLE 4

50 mg of the immunostimulatory peptide obtained by the same method as in Example 2 were dissolved in a mixture of 5 g of methylcellulose and 1000 ml of purified water, and an immunostimulatory agent was produced.

EXAMPLE 5

100 mg of the immunostimulatory peptide obtained by the same method as in Example 1 were dissolved in a mixture of 200 ml of ethyl alcohol and 800 ml of purified water, and an immunostimulatory agent was produced.

EXAMPLE 6

A mouth wash with the following composition was produced. This mouth wash is 50 to 100 times diluted with water at the time of use.

| Ethyl alcohol | 20.0 g |
|---|---|
| Saccharin sodium | 3.0 g |
| Immunostimulatory peptide of Example 1 | 0.1 g |
| Purified water | 76.0 ml |

EXAMPLE 7

An eye drop with the following composition was produced.

| Boric acid | 1.9 g |
|---|---|
| Immunostimulatory peptide of Example 1 | 0.02 g |
| Methylcellulose | 0.5 g |
| Purified water | 97.4 g |

EXAMPLE 8

A dermatological spray with the following composition was produced.

| Propylene glycol | 0.4 g |
|---|---|
| Ethyl alcohol | 3.5 g |
| Freon 11 (trademark; manufactured by duPont Co.; trichlorofluoromethane) | 30.0 g |
| Freon 12 (trademark;; manufactured by duPont co.; dichlorodifluoromethane) | 48.0 g |
| Diethyl ether | 16.0 g |
| Immunostimulatory peptide of Example 1 | 0.1 g |

INDUSTRIAL APPLICATION

The peptide is useful as an immunostimulatory agent for prevention and treatment of bacterial, fungal, and vital infections in humans and animals.

We claim:

1. A medicament for promoting the release of leukotriene B4 from polymorphonuclear neutrophils or histamine from mast cells in animals or humans comprising effective amounts of a substantially purified and isolated peptide having the amino acid sequence: Phe-Lys-Cys-Arg-Arg-Trp-Gln-Trp-Arg-Met-Lys-Lys-Leu-Gly-Ala-Pro-Ser-Ile-Thr-Cys-Val-Arg-Arg-Ala-Phe to accomplish said release of leukotriene B4 and histamine, or derivatives of said peptide having minor amino acid substitutions which do not abolish the capacity of the peptide to release leukotriene B4 and histamine, and a pharmacologically acceptable carrier therefor.

2. A medicament according to claim 1 wherein the substantially purified and isolated peptide has the amino acid sequence Phe-Lys-Cys-Arg-Arg-Trp-Gln-Trp-Arg-Met-Lys-Lys-Leu-Gly-Ala-Pro-Ser-Ile-Thr-Cys-Val-Arg-Arg-Ala-Phe.

3. A medicament according to claim 1 wherein the peptide or derivative thereof is present in the medicament in a concentration of at least 1 ppm by weight.

4. A medicament according to claim 1 wherein the peptide or derivative thereof is present in a concentration of 10 to 100 ppm by weight.

5. A medicament according to claim 2 wherein the peptide is present in a concentration of at least 1 ppm by weight.

6. A medicament according to claim 2 wherein the peptide is present in a concentration of 10 to 100 ppm by weight.

7. A method of promoting the release of leukotriene B4 from polymorphonuclear neutrophils or histamine from mast cells in animals or humans which comprises administering to a patient effective amounts of a substantially purified and isolated peptide having the amino acid sequence: Phe-Lys-Cys-Arg-Arg-Trp-Gln-Trp-Arg-Met-Lys-Lys-Leu-Gly-Ala-Pro-Ser-Ile-Thr-Cys-Val-Arg-Arg-Ala-Phe to accomplish said release of leukotriene B4 and histamine or derivatives of said peptide having minor amino acid substitutions which do not abolish the capacity of the peptide to release leukotriene B4 and histamine.

8. A method according to claim 7 wherein the substantially purified and isolated peptide has the amino acid sequence Phe-Lys-Cys-Arg-Arg-Trp-Gln-Trp-Arg-Met-Lys-Lys-Leu-Gly-Ala-Pro-Ser-Ile-Thr-Cys-Val-Arg-Arg-Ala-Phe.

9. A method according to claims 7 or 8 wherein the substantially purified and isolated peptide or derivative thereof is administered as an active ingredient in a medicament in combination with a pharmaceutically acceptable carrier.

10. A method according to claim 9 wherein the substantially purified and isolated peptide or derivative thereof is administered in a concentration of at least 1 ppm by weight, based on the weight of the medicament.

11. A method according to claim 9 wherein the substantially purified and isolated peptide or derivative thereof is administered at a concentration of 10 to 100 ppm by weight.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 25 amino acids (B) TYPE: amino acid
(C) STRANDEDNESS: single
(D) TOPOLOGY: linear (xi) SEQUENCE DESCRIPTION: SEQ ID NO:1:

Phe Lys Cys Arg Arg Trp Gln Trp Arg Met Lys Lys Leu Gly Ala
1               5                   10                  15

Pro Ser Ile Thr Cys Val Arg Arg Ala Phe
                20                  25